United States Patent
Nickel et al.

[11] Patent Number: 5,591,377
[45] Date of Patent: *Jan. 7, 1997

[54] VISCOUS WATER-BASED SURFACTANT PREPARATION

[75] Inventors: Dieter Nickel, Erkrath; Rainer Hofmann, Duesseldorf, both of Germany

[73] Assignee: Henkel Kommanditgesellschaft auf Aktien, Duesseldorf, Germany

[*] Notice: The portion of the term of this patent subsequent to Nov. 29, 2013, has been disclaimed.

[21] Appl. No.: 515,024

[22] Filed: Aug. 14, 1995

Related U.S. Application Data

[63] Continuation of Ser. No. 211,852, filed as PCT/EP92/02310, Oct. 7, 1992, abandoned.

[30] Foreign Application Priority Data

Oct. 15, 1991 [DE] Germany .......................... 41 34 077.9

[51] Int. Cl.$^6$ .............................. C11D 17/00; C11D 1/12; C11D 1/755
[52] U.S. Cl. ............................. 510/383; 510/336
[58] Field of Search ............................ 252/173, 174.17, 252/174.18, 549, 550, 553, 554, DIG. 14

[56] References Cited

U.S. PATENT DOCUMENTS

| | | | |
|---|---|---|---|
| 3,547,828 | 12/1970 | Mansfield et al. | 252/351 |
| 4,396,520 | 8/1983 | Payne et al. | 252/89.1 |
| 4,732,696 | 3/1988 | Urfer | 254/174.17 |
| 5,138,046 | 8/1992 | Wuest | 536/18.6 |
| 5,258,142 | 11/1993 | Giesen et al. | 252/552 |

FOREIGN PATENT DOCUMENTS

| | | | |
|---|---|---|---|
| 0070074 | 1/1983 | European Pat. Off. | C11D 1/83 |
| 0092355 | 10/1983 | European Pat. Off. | C07H 15/04 |
| 0092877 | 11/1983 | European Pat. Off. | C11D 1/83 |
| 0105556 | 4/1984 | European Pat. Off. | C11D 3/22 |
| 0132046 | 1/1985 | European Pat. Off. | C07H 15/04 |
| 0132043 | 1/1985 | European Pat. Off. | C07H 15/04 |
| 0301298 | 2/1989 | European Pat. Off. | C07H 15/04 |
| 0306843 | 3/1989 | European Pat. Off. | A61K 7/08 |
| 0355551 | 2/1990 | European Pat. Off. | C11D 1/83 |
| 0357969 | 3/1990 | European Pat. Off. | C07H 15/04 |
| 0362671 | 4/1990 | European Pat. Off. | C07H 15/04 |
| 1278421 | 6/1972 | United Kingdom | C07C 143/18 |
| 8602943 | 5/1986 | WIPO | C11D 17/00 |
| 9006300 | 7/1988 | WIPO | B01F 17/10 |

OTHER PUBLICATIONS

A. M. Schwartz, J. W. Perry, Surface Active Agents, vol. 1, Interscience Publishers, 1949, Seite 372 (month not available).

*Primary Examiner*—Glenn A. Caldarola
*Assistant Examiner*—Patricia L. Hailey
*Attorney, Agent, or Firm*—Wayne C. Jaeschke; John E. Drach; Henry E. Millson, Jr.

[57] ABSTRACT

The stability in storage and flowability of liquid water-based alkyl glycoside preparations of relatively low concentration were to be improved and their handling under in-use conditions was to be facilitated by an increase in viscosity with very small quantities of non-alkyl-glycoside active substance. This was achieved by gel-form aqueous mixtures consisting essentially of 2% by weight to 15% by weight of an alkyl glycoside corresponding to the formula $R^1$—$O(G)_n$, in which $R^1$ is an alkyl radical containing 8 to 22 C atoms, G is a glycose unit and n is a number of 1 to 10, 0.05% by weight to 2% by weight of an anionic surfactant of the sulfate or sulfonate type, the ratio by weight of alkyl glycoside to sulfate and/or sulfonate being 40:1 to 5:1, and 83% by weight to 97.95% by weight water or a mixture of water with a water-miscible organic solvent.

20 Claims, No Drawings

VISCOUS WATER-BASED SURFACTANT PREPARATION

This application is a continuation of application Ser. No. 08/211,852, filed as PCT/EP92/02310 on Oct. 7, 1992, now abandoned.

BACKGROUND OF THE INVENTION

1. Field of the Invention

This invention relates to low-concentration, high-viscosity water-based surfactant preparations containing alkyl glycosides and certain anionic surfactants, to a process for their production and to their use as detergents or cleaning preparations.

2. Statement of Related Art

It is well known that alkyl glycosides containing long-chain alkyl groups belong to the class of nonionic surfactants. It is also known, as described for example in A. M. Schwartz, J. W. Perry, Surface Active Agents, Vol. I, Interscience Publishers, 1949, page 372, that surfactant mixtures generally have synergistic effects and often show better cleaning properties than would be obtained from the sum of the values of the individual components.

Detergents containing alkyl glycosides in combination with at least one typical anionic surfactant in a ratio of 1:10 to 10:1 are described in European patent application EP 070 074. Detergents containing alkyl glycosides and anionic surfactants are also known from European patent application EP 092 877. In addition, European application EP 105 556 describes liquid detergents containing alkyl glycosides, certain other nonionic surfactants and anionic surfactants. Liquid detergents containing alkyl glycosides in combination with typical anionic surfactants are known from International patent application EO 86/02943. European patent application EP 132 043 describes a process for the production of alkyl glycosides using catalytic quantities of an anionic surfactant in its acid form. According to European patent application EP 132 046, this production process is modified by addition of certain bases after the actual reaction for the purpose of neutralizing the catalyst. The alkyl-glycoside-based intermediate products for detergents or cleaning preparations which are mentioned in these documents are aqueous solutions or pastes of relatively high concentration because the components to be mixed to form the final detergents or cleaning preparations are expected to have a high active substance content. At the same time, they are expected to be easy to handle, in other words they should have a low viscosity and should be flowable and readily pumpable. By contrast, water-based liquid products used by the consumer, including in particular liquid detergents, dishwashing detergents and universal cleaners, but also cosmetic products, for example hair shampoos or body lotions, are expected to show a certain minimum viscosity although, in general, the active substance content of such products is relatively low. Accordingly, products of the type in question normally contain thickeners which generally have the disadvantage that they themselves do not make any contribution towards the cleaning performance of the surfactant component present in the products. Typical thickeners are inorganic water-soluble salts, more particularly sodium chloride, and salts of non-surface-active aromatic sulfonic acids, for example sodium cumenesulfonate.

Organic thickeners are, typically, fatty acid alkanolamides, such as coconut oil fatty acid monoethanolamide, lauric acid monoethanolamide, oleic acid diethanolamide and coconut oil fatty acid diethanolamide, polyethylene glycol difatty acid esters and a number of water-soluble polymers.

In most cases, it is either not possible or is only possible using high concentrations to build up the required viscosity in the surfactant solution solely through the use of inorganic salts. Accordingly, organic thickeners, which are attended by a number of disadvantages, have to be used in addition to the inorganic salts. Thus, solutions thickened with polyethylene glycol fatty acid diesters often show inadequate viscosity stability in storage while water-soluble polymers are often difficult to dissolve and give rise to unwanted flow behavior.

In European patent application EP 306 843, it is proposed to use adducts of ethylene oxide and/or propylene oxide with unsaturated fatty alcohols for the purpose of thickening surfactant solutions. Although these products do not have any of the disadvantages mentioned above, there is still a need for thickeners having comparable properties for an increased thickening effect. This would make it possible to produce systems of relatively high viscosity for a given thickener content and to reduce the thickener content for a predetermined viscosity.

The problem addressed by the present invention was to provide a storable, liquid, flowable water-based alkyl glycoside preparation which, through its relatively high viscosity, would be easy to handle under in-use conditions and which would contain very small quantities of non-alkyl glycoside active substance.

This problem has been solved by a water-based mixture of certain quantities of alkyl glycoside and a certain anionic surfactant.

DESCRIPTION OF THE INVENTION

The surfactant preparations according to the invention are gel-formwater-based mixtures consisting essentially of 2% by weight to 15% by weight of an alkyl glycoside corresponding to formula I $$R^1\text{—}O(G)_n \qquad (I)$$

in which $R^1$ is an alkyl radical containing 8 to 22 carbon atoms, G is a glycose unit and n is a number of 1 to 10, 0.05% by weight to 2% by weight of an anionic surfactant of the sulfate or sulfonate type selected from the group consisting of alkyl sulfates, alkane sulfonates, α-sulfofatty acids, carboxylic acid esters thereof with $C_{1-4}$ alcohols, sulfonation products of alkenes or unsaturated fatty acids and mixtures thereof, the ratio by weight of alkyl glycoside corresponding to formula I to sulfate and/or sulfonate being 40:1 to 5:1, and 83% by weight to 97.95% by weight water.

In the context of the invention, gel-form preparations are understood to be structured, isotropic viscoelastic solutions having a viscoelastic network structure built up of rodlet micelles. They preferably have a viscosity, as measured at temperatures of 20° C. to 25° C. at a shear rate of 10 s$^{-1}$, in the range from 250 mPa.s to 10,000 mPa.s and more particularly in the range from 600 mPa.s to 7,000 mPa.s.

In a preferred embodiment, the alkyl glycoside preparations according to the invention contain 3% by weight to 12% by weight and, more particularly, 4% by weight to 10% by weight alkyl glycoside corresponding to formula I, 0.075% by weight to 2.5% by weight and, more particularly, 0.1% by weight to 2% by weight anionic surfactant and, as the balance to 100% by weight, water. Part of the water, preferably no more than 2% by weight, based on the preparation according to the invention as a whole, may be replaced by a water-miscible organic solvent, preferably from the group consisting of alcohols containing 1 to 4 carbon atoms, glycols containing 2 to 4 carbon atoms and the diglycols and triglycols derivable therefrom and also the corresponding glycol ethers and mixtures of the substances mentioned.

The present invention also relates to a process for the production of storable, water-based gel-form surfactant preparations, which have a viscosity of 250 mPa.s to 10,000 mPa.s at temperatures of 20° to 25° C. and at a shear rate of 10 s$^{-1}$, by mixing an aqueous solution containing an alkyl glycoside corresponding to formula I

$$R^1—O(G)_n \qquad (I)$$

in which $R^1$ is an alkyl radical containing 8 to 22 carbon atoms, G is a glycose unit and n is a number of 1 to 10, with an anionic surfactant of the sulfate or sulfonate type selected from the group consisting of alkyl sulfates, alkane sulfonates, α-sulfofatty acids, carboxylic acid esters thereof, sulfonation products of alkenes or unsaturated fatty acids and mixtures thereof in a ratio by weight of alkyl glycoside corresponding to formula I to sulfate and/or sulfonate of 40:1 to 5:1 and with water in such a quantity that the total surfactant content in the preparation is 2.2% by weight to 15% by weight.

To this end, a water-based paste containing alkyl glycoside corresponding to formula I in a concentration of 30% by weight to 60% by weight is preferably mixed with an aqueous solution containing at least one of the above-mentioned anionic surfactants in such a quantity that the sum of the surfactants in the resulting water-based preparation is 2.5% by weight to 10% by weight and the resulting gel contains 90% by weight to 97.5% by weight water. In principle, the water may be added at any stage during the production of the preparations according to the invention if the starting materials used do not already contain enough of this solvent. The components are preferably heated to temperatures of 60° C. to 80° C. and are mixed in typical mixers which are preferably heatable and which are kept in particular at temperatures in the range mentioned throughout the mixing process.

The alkyl glycosides suitable for the surfactant preparations according to the invention and their production are described, for example, in European patent applications EP 92 355, EP 301 298, EP 357 969 and EP 362 671 or in U.S. Pat. No. 3,547,828. The glycoside components ($(G)_n$ in formula I) of these alkyl glycosides are oligomers or polymers of naturally occurring aldose or ketose monomers, including in particular glucose, mannose, fructose, galactose, talose, gulose, altrose, allose, idose, ribose, arabinose, xylose and lyxose. The oligomers consisting of these glycoside-bonded monomers are characterized not only by the type of sugars present in them, but also by their number, the so-called degree of oligomerizartion. As an analytically determined quantity, the degree of oligomerization (n in formula I) may also be a broken number and is generally between 1 and 10 and, in the case of the alkyl glycosides preferably used, is below 1.5 and, more particularly, between 1.2 and 1.4. By virtue of its ready availability, glucose is the preferred monomer unit.

The alkyl component ($R^1$ in formula I) of the alkyl glycosides present in the surfactant preparations according to the invention also preferably emanates from readily accessible derivatives of renewable raw materials, more particularly from fatty alcohols, although branches-chain isomers thereof, more particularly so-called oxoalcohols, may also be used for the preparation of suitable alkyl glycosides. Accordingly, primary alcohols containing linear octyl, decyl, dodecyl, tetradecyl, hexadecyl and octadecyl radicals and mixtures thereof are particularly useful. Particularly suitable alkyl glycosides contain a coconut oil fatty alkyl radical, i.e. mixtures in which, essentially, $R^1$=dodecyl and $R^1$=tetradecyl.

From their production, the alkyl glycosides may contain small quantities, for example 1 to 2%, of unreacted free fatty alcohol which, in general, does not adversely affect the properties of the preparations produced with them.

The alkyl sulfates suitable for use in accordance with the invention are known anionic surfactants which are generally produced by reaction of aliphatic primary alcohols with a sulfating agent, for example sulfur trioxide or chlorosulfonic acid, and subsequent neutralization and hydrolysis of the reaction products formed, preferably with alkali metal, ammonium or alky- or hydroxyalkyl-substituted ammonium bases. Alkyl sulfates suitable for use in the process according to the invention are preferably derived from fatty alcohols containing 12 to 22 carbon atoms and, more particularly, 12 to 18 carbon atoms. Typical examples are lauryl alcohol, myristyl alcohol, cetyl alcohol, stearyl alcohol or behenyl alcohol. The alkyl sulfates may also be derived from technical alcohol mixtures, for example of the type formed in the hydrogenation of technical fatty acid ester mixtures of natural origin or aldehydes from Roelen's oxo synthesis. Alkyl sulfates based on technical coconut oil or tallow fatty alcohol cuts are preferred.

Due to the content of unsaturated alcohols in the starting material used for the sulfation reaction, alkyl sulfates of the type in question may also contain more or less large quantities of sulfonation products of mono-, di- or triunsaturated alcohols having the above-mentioned chain lengths. Because the sulfation reaction can also be accompanied by addition of the sulfating agent onto the double bond where unsaturated alcohols are used, the alkyl sulfates are generally mixtures of alkenyl sulfates with substances containing an internal sulfonate group or a sulfonate group and a sulfate group. In the context of the invention, therefore, the term "alkyl sulfate" also encompasses mixtrues such as these. Where they are present in the alkyl sulfate, sulfonation products emanating from unsaturated alcohols are preferably present in quantities of not more than 80% by weight and, more particularly, in quantities of 30% by weight to 70% by weight in the alkyl sulfate used, based on the total anionic surfactant active substance present therein.

The sulfofatty acid salts suitable for incorporation in the preparations according to the invention are neutralized derivatives of $C_{8-22}$ fatty acids containing at least one double bond, including in particular the sulfonation products of lauroleic acid, myristoleic acid, palmitoleic acid, oleic acid, gadoleic acid and erucic acid. Sulfofatty acid salts such as these are prepared by reaction of the unsaturated fatty acids with a sulfonating agent and subsequent neutralization and hydrolysis with the aqueous bases mentioned by known methods such as described, for example, in GB 1,278,421 or in International patent application WO 90/06300. This results in the formation of mixtures of the saturated fatty acids bearing one sulfo group and one hydroxy group with unsaturated fatty acids bearing one sulfo group formed therefrom by formal elimination of 1 mol equivalent of water. Surface-active mixtures of hydroxyalkyl sulfonates with alkene sulfonates can be produced by an analogous reaction from alkenes preferably containing 12 to 22 carbon atoms.

α-Sulfofatty acid salts can be produced by reaction of $C_{6-22}$ and preferably $C_{16-18}$ fatty acids preferably having an iodine number below 20 with a sulfonating agent and subsequent neutralization with aqueous bases. The sulfonating agent used in this case is, in particular, sulfuric acid, oleum, chlorosulfonic acid or gaseous sulfur trioxide in admixture with an inert gas. Suitable neutralization bases are, above all, aqueous solutions of alkali metal and alkaline earth metal hydroxides or ammonia. Alternatively, esters of fatty acids of the type mentioned with $C_{1-4}$ alcohols, more particularly fatty acid methyl esters, may be sulfonated, in which case the α-sulfofatty acid esters suitable for use in accordance with the invention are formed. By using aqueous base in excess and eliminating methanol, they can be saponified to the corresponding α-sulfofatty acid salts and neutralized. Typical examples of fatty acids of the type mentioned are caproic acid, caprylic acid, capric acid, lauric acid, myristic acid or behenic acid. Substances having particularly favorable detergent properties are obtained on the basis of palmitic acid and stearic acid which are preferred for these reasons. These fatty acids may also be present in the form of technical mixtures of the type typically formed in the hydrolysis of vegetable or animal fatty acid glycerol esters. If mixtures such as these have high percentage contents of unsaturated fatty acids, they may be converted in known manner by hydrogenation, for example in the presence of nickel catalysts, into mixtures of substantially saturated fatty acids having an iodine value below 20.

The alkane sulfonates suitable for use in accordance with the invention are substances which are obtained by sulfoxidation of hydrocarbons preferably containing 10 to 20 carbon atoms. Products in which the sulfonic acid substituents are statistically distributed are formed and, if desired, may be separated in known manner. Secondary alkane sulfonates containing 12 to 17 C atoms are particularly suitable for the mixtures according to the invention. In this case, two, suitable cations are, in particular, cations from the group of alkali metal ions, ammonium ions or alkyl- or hydroxyalkyl-substituted ammonium ions.

The anionic surfactants mentioned have long been known as particularly effective. However, it was surprising to find that the viscosity of dilute aqueous alkyl glycoside solutions could be significantly increased by the addition of very small quantities of such anionic surfactants. By contrast, the viscosity of dilute aqueous alkyl glycoside solutions decreases through the addition of other anionic surfactants, for example alkylbenzene sulfonate. Accordingly, alkylbenzene sulfonates cannot be used for the purposes of the present invention although they are known to be extremely effective anionic surfactants.

The surfactant preparations according to the invention have excellent cleaning properties and show high solubility in cold water. Accordingly, they are preferably used as laundry detergents, dishwashing detergents or cleaning preparations and in hair and body care. Other typical constituents of such preparations, including in particular builders, such as zeolites and layer silicates, corrosion inhibitors, bleaches, bleach activators, optical brighteners, enzymes, redeposition inhibitors, antimicrobial agents, abrasives, foam stabilizers, preservatives, pH regulators, opacifiers and pearlescers, dyes and fragrances and also additional surfactants, may be added to the preparations according to the invention.

EXAMPLES

Example 1

Aqueous mixtures of the anionic surfactants listed in Tables 1 (sum of the surfactant components 5% by weight) and 2 (sum of the surfactant components 10% by weight) with $C_{12-14}$ alkyl glycoside (degree of oligomerization 1.4) in the mixing ratios (alkyl glycoside to anionic surfactant) shown had the following viscosities (at 25° C., as measured with a Carri-Med® CS 100 shear-strain-controlled rotational rheometer at a shear rate of 10 $s^{-1}$):

TABLE 1

Viscosity of 5% by weight preparations (25° C.)

| Anionic surfactant | Mixing ratio [% by weight] | Viscosity [mPa · s] |
|---|---|---|
| — | 5:0 | 320 |
| Sulfopon T[a] | 4.9:0.1 | 1090 |
|  | 4.75:0.25 | 1560 |
|  | 4.5:0.5 | 1560 |
| Sulfopon K[b] | 4.9:0.1 | 770 |
|  | 4.5:0.5 | 1000 |
| Sulfoester[c] | 4.9:0.1 | 620 |
|  | 4.75:0.25 | 1780 |
|  | 4.5:0.5 | 1200 |
| Na—$C_{16}$-alkyl sulfate | 4.9:0.1 | 930 |
|  | 4.75:0.25 | 1940 |
|  | 4.5:0.5 | 4530 |

[a]: Na $C_{16/18}$ alkyl sulfate, a product of Henkel KGaA
[b]: Na lauryl sulfate, a product of Henkel KGaA
[c]: Na salt of an α-sulfonated $C_{16/18}$ fatty acid methyl ester mixture, a product of Henkel KGaA

TABLE 2

Viscosity of 10% by weight preparations (25° C.)

| Anionic surfactant | Mixing ratio [% by weight] | Viscosity [mPa · s] |
|---|---|---|
| — | 10:0 | 720 |
| Sulfopon T[a] | 9.9:0.1 | 1010 |
|  | 9.5:0.5 | 2450 |
|  | 9:1 | 4380 |
| Sulfopon K[b] | 9.9:0.1 | 830 |
|  | 9.5:0.5 | 1730 |
|  | 9:1 | 4980 |
| Sulfoester[c] | 9.9:0.1 | 830 |
|  | 9.5:0.5 | 1890 |
|  | 9:1 | 6950 |
| Na—$C_{16}$-alkyl sulfate | 9.9:0.1 | 1340 |
|  | 9.75:0.25 | 1510 |
|  | 9.5:0.5 | 1780 |
|  | 9:1 | 4300 |

[a]: Na $C_{16/18}$ alkyl sulfate, a product of Henkel KGaA
[b]: Na lauryl sulfate, a product of Henkel KGaA
[c]: Na salt of an α-sulfonated $C_{16/18}$ fatty acid methyl ester mixture, a product of Henkel KGaA Other preparations containing $C_{12/14}$ alkyl glucoside and NA $C_{11/13}$ alkyl benzenesulfonate (Maranil®, a product of Hüls) were prepared and tested for comparison. These comparison preparations, which did not correspond to the invention, had a viscosity of 270 mPa.s in 5% by weight solution (ratio by weight 4.9:0.1) and 360 mPa.s in 10% by weight solution (ratio by weight 9:1).

What is claimed is:

1. A viscous surfactant composition of low concentration in the form of a gel-like water-based mixture consisting essentially of:

(a) from about 2% by weight to about 15% by weight of an alkyl glycoside corresponding to the formula I $$R^1\text{—}O(G)_n \qquad (I)$$

wherein $R^1$ is an alkyl radical having from about 8 to about 22 carbon atoms, G is a glycose unit and n is a number of 1 to 10;

(b) from about 0.05% by weight to about 2% by weight of an anionic surfactant of the sulfate or sulfonate type selected from the group consisting of an alkyl sulfate, an alkane sulfonate, an ∝-sulfo fatty acid salt, a carboxylic acid ester of an ∝-sulfofatty acid with a $C_{1-4}$ alcohol, the neutralized sulfonation product of an alkene or $C_{8-22}$ unsaturated fatty acid and, mixtures thereof;

wherein the weight ratio of said alkyl glycoside to said anionic surfactant is from about 40:1 to about 5:1, and wherein said composition contains from about 83% by weight to about 97.95% by weight water.

2. The surfactant composition of claim 1 wherein the viscosity of said composition is from about 250 mPas to about 10,000 mPas at 20° C. to 25° C. and at a shear rate of 10 $s^{-1}$.

3. The surfactant composition of claim 1 wherein the viscosity of said composition is from about 600 mPas to about 7,000 mPas, at 20° C. to 25° C. and at a shear rate of 10 $s^{-1}$.

4. The surfactant composition of claim 1 wherein said anionic surfactant is an alkyl sulfate having a linear $C_{12-18}$ alkyl group.

5. The surfactant composition of claim 4 wherein said alkyl sulfate contains no more than 80% by weight sulfonation products of unsaturated alcohols, based on the total anionic surfactant active substance present therein.

6. The surfactant composition of claim 5 wherein said alkyl sulfate contains from about 30% to about 70% by weight sulfonation products of unsaturated alcohols, based on the total anionic surfactant active substance present therein.

7. The surfactant composition of claim 1 wherein said anionic surfactant is an alkane sulfonate having a $C_{10-20}$ alkyl group.

8. The surfactant composition of claim 7 wherein said anionic surfactant is an alkane sulfonate having a secondary $C_{12-17}$ alkyl group.

9. The surfactant composition of claim 1 wherein said anionic surfactant is the neutralized sulfonation product of a $C_{8-22}$ unsaturated fatty acid having at least one double bond.

10. The surfactant composition of claim 1 wherein said anionic surfactant is an α-sulfo fatty acid or a carboxylic acid ester of an α-sulfofatty acid with a $C_{1-4}$ alcohol, wherein the fatty acid contains form 6 to 22 carbon atoms.

11. The surfactant composition of claim 10 wherein the fatty acid in said α-sulfo fatty acid or a carbonxylic acid ester of an α-sulfofatty acid with a $C_{1-4}$ alcohol has from 16 to 18 carbon atoms.

12. The surfactant composition of claim 1 wherein said anionic surfactant is a neutralized sulfonation product of an alkene having from about 12 to about 22 carbon atoms.

13. The surfactant composition of claim 1 wherein component (a) is present in from about 3% to about 12% by weight.

14. In a laundry detergent, dishwashing detergent, cleaning preparation, hair-care preparation or body-care preparation, the improvement wherein the surfactant composition of claim 13 is present therein.

15. The surfactant composition of claim 1 wherein component (a) is present in from about 4% to about 10% by weight, and component (b) is present in from about 0.1% to about 2% by weight.

16. The surfactant composition of claim 1 wherein up to 2% by weight of water, based on the weight of the composition, is replaced by a water-miscible solvent.

17. In a laundry detergent, dishwashing detergent, cleaning preparation, hair-care preparation, or body-care preparation, the improvement wherein the surfactant composition of claim 1 is present therein.

18. A process for the production of storable, water-based gel-foam surfactant composition having a viscosity of from about 250 mPa.s to about 10,000 mPa.s at a temperature of 20° C. to 25° C. and at a shear rate of 10 $s^{-1}$ which comprises mixing an aqueous solution consisting essentially of:

(a) an alkyl glycoside corresponding to formula l $$R^1\text{—O}(G)_n \qquad (1)$$

wherein $R^1$ is an alkyl radical having from about 8 to about 22 carbon atoms, G is a glycose unit and n is a number of 1 to 10:

(b) an anionic surfactant of the sulfate or sulfonate type selected from the group consisting of an alkyl sulfate, an alkane sulfonate, an α-sulfo fatty acid, a carboxylic acid ester of an α-sulfofatty acid with a $C_{1-4}$ alcohol, the neutralized sulfonation product of an alkene or $C_{8-22}$ unsaturated fatty acid and, mixtures thereof;

wherein the weight ratio of said alkyl glycoside to said anionic surfactant is from about 40:1 to about 5:1 with water in such a quantity that the total surfactant content in the preparation is 2.2% by weight to 15% by weight.

19. The process of claim 18 wherein a water-based paste containing component (a) in a concentration of from about 30% to about 60% by weight is mixed with an aqueous solution of component (b) in such a quantity that the sum of components (a) and (b) in the resulting gel-form surfactant composition is from about 2.5% to about 10% by weight, and the composition contains from about 90% to about 97.5% by weight of water.

20. The process of claim 19 wherein the process is carried out at a temperature in the range of from about 60° C. to about 80° C.

* * * * *